(12) United States Patent
Schlesinger et al.

(10) Patent No.: US 9,870,678 B2
(45) Date of Patent: Jan. 16, 2018

(54) DYNAMIC ALARM SYSTEM FOR REDUCING ALARM FATIGUE

(71) Applicant: Vanderbilt University, Nashville, TN (US)

(72) Inventors: Joseph Schlesinger, Nashville, TN (US); Allyson Garcia, Nashville, TN (US); Victoria Mitchell, Nashville, TN (US); Forbes Turley, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/228,856

(22) Filed: Aug. 4, 2016

(65) Prior Publication Data

US 2017/0039822 A1    Feb. 9, 2017

Related U.S. Application Data

(60) Provisional application No. 62/200,935, filed on Aug. 4, 2015, provisional application No. 62/326,226, filed on Apr. 22, 2016, provisional application No. 62/326,480, filed on Apr. 22, 2016.

(51) Int. Cl.
| | |
|---|---|
| *G08B 3/10* | (2006.01) |
| *H03G 3/32* | (2006.01) |
| *A61B 5/00* | (2006.01) |
| *A61B 5/0205* | (2006.01) |
| *A61B 5/021* | (2006.01) |
| *A61B 5/024* | (2006.01) |
| *A61B 5/0402* | (2006.01) |
| *A61B 5/145* | (2006.01) |

(52) U.S. Cl.
CPC ............ *G08B 3/10* (2013.01); *A61B 5/02055* (2013.01); *A61B 5/746* (2013.01); *H03G 3/32* (2013.01); *A61B 5/021* (2013.01); *A61B 5/024* (2013.01); *A61B 5/0402* (2013.01); *A61B 5/14542* (2013.01); *A61B 2560/0242* (2013.01)

(58) Field of Classification Search
CPC ...... A61B 5/746; A61B 5/02055; G08B 3/10; H03G 3/32
See application file for complete search history.

(56) References Cited

U.S. PATENT DOCUMENTS

| | | | |
|---|---|---|---|
| 2,338,551 | A | 1/1944 | Stanko |
| 3,579,233 | A | 5/1971 | Raschke |
| 5,077,799 | A | 12/1991 | Cotton |
| 5,666,426 | A | 9/1997 | Helms |
| 2005/0046575 | A1 | 3/2005 | Cooper et al. |

(Continued)

OTHER PUBLICATIONS

Top 10 health technology hazards for 2013. Health Devices. 2012;41(11):342-365.

(Continued)

*Primary Examiner* — Leon Flores
(74) *Attorney, Agent, or Firm* — Michael Best & Friedrich LLP

(57) ABSTRACT

A dynamic alarm system that can assess the background noise in a clinical environment with sub-minute time sampling and change the alarm output to a desired signal-to-noise ratio (SNR) below ambient noise (negative SNR) to minimize clinician fatigue and ameliorate deleterious patient outcomes, while preserving clinician performance.

14 Claims, 12 Drawing Sheets

(56) References Cited

U.S. PATENT DOCUMENTS

| | | | | |
|---|---|---|---|---|
| 2011/0261983 A1* | 10/2011 | Claussen | ............ | H04R 25/505 381/317 |
| 2015/0016633 A1* | 1/2015 | Gao | ........................ | H03G 3/20 381/107 |

OTHER PUBLICATIONS

Logan MK. Signal to noise. Biomed. Instrum. Technol. 2011;Suppl:1.

Occupational Safety and Health Administration. United States Department of Labor. https://www.osha.gov/SLTC/noisehearingconservation/ Accessed Dec. 3, 2014.

Choiniere DB. The effects of hospital noise. Nurs. Adm. Q. 2010;34(4):327-333.

Occupational Safety and Health Administration—Employee Alarm Systems. Part No. 1910. Subpart L. Standard No. 1910.165. United States Department of Labor.

Ross LA, Saint-Amour D, Leavitt VM, Javitt DC, Foxe JJ. Do you see what I am saying? Exploring visual enhancement of speech comprehension in noisy environments. Cereb. Cortex. 2007;17(5):1147-1153.

Stevenson RA, Wallace MT. Multisensory temporal integration: task and stimulus dependencies. Exp. Brain Res. 2013;227(2):249-261.

Diederich A, Colonius H. Bimodal and trimodal multisensory enhancement: effects of stimulus onset and intensity on reaction time. Percept. Psychophys. 2004;66(8):1388-1404.

Edworthy J, Hellier E. Fewer but better auditory alarms will improve patient safety. Qual Saf Health Care. 2005;14(3):212-215.

Joint Commission—Medical device alarm safety in hospitals. Sentinel Event Alert. 2013(50):1-3.

American College of Clinical Engineering Healthcare Technology Foundation. Impact of clinical alarms on patient safety. 2006.

Cvach M. Monitor alarm fatigue: an integrative review. Biomed. Instrum. Technol. 2012;46(4):268-277.

Schlesinger JJ, Stevenson RA, Wallace MT. Improving pulse oximetry pitch perception with multisensory perceptual training. Anesth. & Analg. Jun. 2014;118(6):1249-1253.

Stevenson RA, Schlesinger JJ, Wallace MT. Effects of divided attention and operating room noise on perception of pulse oximeter pitch changes: a laboratory study. Anesthesiology. 2013;118(2):376-381.

Grumet GW. Pandemonium in the modern hospital. N. Engl. J. Med. 1993;328(6):433-437.

Xie H, Kang J, Mills GH. Clinical review: The impact of noise on patients' sleep and the effectiveness of noise reduction strategies in intensive care units. Crit. Care. 2009;13(2):208.

Kamdar BB, Needham DM, Collop NA. Sleep deprivation in critical illness: its role in physical and psychological recovery. J. Intensive Care Med. 2012;27(2):97-111.

Association for the Advancement of Medical Instrumentation Foundation Healthcare Technology Safety Institute. The Joint Commission's National Patient Safety Goal on Alarm Management: How Do We Get Started? 2013.

Stevenson RA, Fister JK, Barnett ZP, Nidiffer AR, Wallace MT. Interactions between the spatial and temporal stimulus factors that influence multisensory integration in human performance. Exp. Brain Res. 2012;219(1):121-137.

Stevenson RA, Siemann JK, Schneider BC, et al. Multisensory temporal integration in autism spectrum disorders. J. Neurosci. 2014;34(3):691-697.

Powers AR, 3rd, Hillock AR, Wallace MT. Perceptual training narrows the temporal window of multisensory binding. J. Neurosci. 2009;29(39):12265-12274.

Stevenson RA, Wilson MM, Powers AR, Wallace MT. The effects of visual training on multisensory temporal processing. Exp. Brain Res. 2013;225(4):479-489.

Powers AR, 3rd, Hevey MA, Wallace MT. Neural correlates of multisensory perceptual learning. J. Neurosci. 2012;32(18):6263-6274.

Purves D. Neuroscience. 5th ed. Ch. 13, pp. 277-302, Sunderland, MA: Sinauer Associates, Inc.; 2012.

Freyman RL, Balakrishnan U, Helfer KS. Effect of number of masking talkers and auditory priming on informational masking in speech recognition. J. Acoust. Soc. Am. 2004;115(5 Pt 1):2246-2256.

Siegwart H, Scherer KR. Acoustic concomitants of emotional expression in operatic singing: the case of Lucia in Ardigliincensi. J. Voice. 1995;9(3):249-260.

Jackson JC, PandharipandePP, Girard TD, et al. Depression, posttraumatic stress disorder, and functional disability in survivors of critical illness in the Brain—ICU study: a longitudinal cohort study. The Lancet. Respiratory medicine. 2014;2(5):369-379.

American Psychiatric Association: Diagnostic and Statistical Manual of Mental Disorders. 5th ed. Arlington, VA: American Psychiatric Association; 2013.

Scragg P, Jones A, Fauvel N. Psychological problems following ICU treatment. Anaesthesia. 2001;56(1):9-14.

Jones C, Griffiths RD, Humphris G, Skirrow PM. Memory, delusions, and the development of acute posttraumatic stress disorder-related symptoms after intensive care. Crit. Care Med. 2001;29(3):573-580.

Jones C, Skirrow P, Griffiths RD, et al. Rehabilitation after critical illness: a randomized, controlled trial. Crit. Care Med. 2003;31(10):2456-2461.

Cuthbertson BH, Hull A, Strachan M, Scott J. Post-traumatic stress disorder after critical illness requiring general care. Intensive Care Med. 2004;30(3):450-455.

Shaw RJ, Harvey JE, Nelson KL, Gunary R, Kruk H, Steiner H. Linguistic analysis to assess medically related posttraumatic stress symptoms. Psychosomatics. 2001;42(1):35-40.

Eddleston JM, White P, Guthrie E. Survival, morbidity, and quality of life after discharge from intensive care. Crit. Care Med. 2000;28(7):2293-2299.

Schelling G, Stoll C, Haller M, et al. Health-related quality of life and posttraumatic stress disorder in survivors of the acute respiratory distress syndrome. Crit. Care Med. 1998;26(4):651-659.

Schelling G, Richter M, Roozendaal B, et al. Exposure to high stress in the intensive care unit may have negative effects on health-related quality-of-life outcomes after cardiac surgery. Crit. Care Med. 2003;31(7):1971-1980.

Rattray JE, Johnston M, Wildsmith JA. Predictors of emotional outcomes of intensive care. Anaesthesia. 2005;60 (11)1085-1092.

Schelling G, Kilger E, Roozendaal B, et al. Stress doses of hydrocortisone, traumatic memories, and symptoms of posttraumatic stress disorder in patients after cardiac surgery: a randomized study. Biol. Psychiatry. 2004;55 (6):627-633.

Kress JP, Gehlbach B, Lacy M, Pliskin N, Pohlman AS, Hall JB. The long-term psychological effects of daily sedative interruption on critically ill patients. Am. J. Respir. Crit. Care Med. 2003;168(12):1457-1461.

Schelling G, Briegel J, Roozendaal B, Stoll C, Rothenhausler HB, Kapfhammer HP. The effect of stress doses of hydrocortisone during septic shock on posttraumatic stress disorder in survivors. Biol. Psychiatry. 2001;50 (12):978-985.

Kapfhammer HP, Rothenhausler HB, Krauseneck T, Stoll C, Schelling G. Posttraumatic stress disorder and health-related quality of life in long-term survivors of acute respiratory distress syndrome. Am. J. Psychiatry. 2004;161 (1):45-52.

Deb S, Claudio D. Alarm fatigue and its influence on staff performance. IIE Transactions on Healthcare Systems Engineering. 2015;5(3):183-196.

* cited by examiner

FIG. 5A
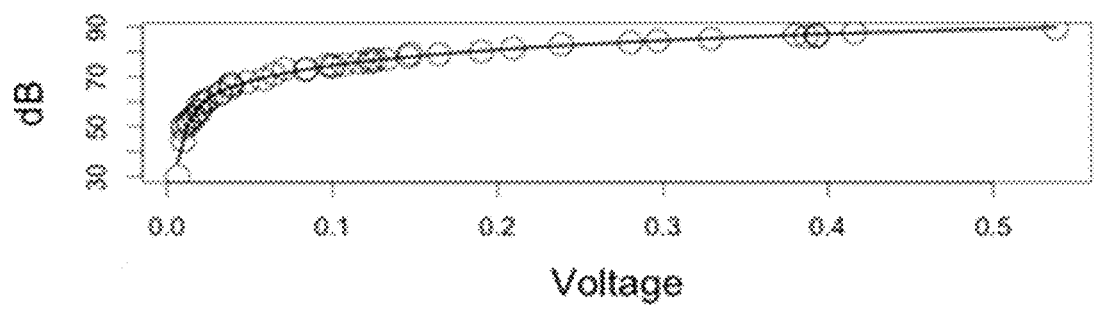
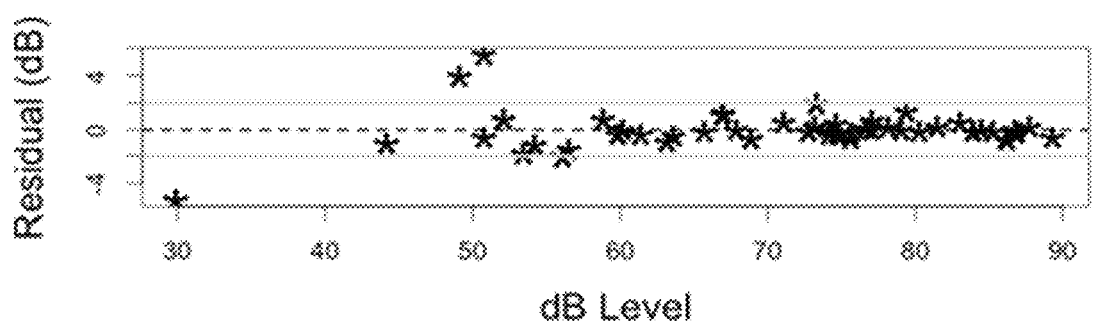
FIG. 5B

DYNAMIC ALARM SYSTEM FOR REDUCING ALARM FATIGUE

CROSS-REFERENCE TO RELATED APPLICATIONS

This application is a non-provisional of and claims benefit of U.S. Provisional Application No. 62/200,935, filed on Aug. 4, 2015; U.S. Provisional Application No. 62/326,226, filed on Apr. 22, 2016; and U.S. Provisional Application No. 62/326,480, filed on Apr. 22, 2016. The contents of these applications are incorporated herein by reference.

BACKGROUND OF THE INVENTION

The intensive care unit (ICU) is characterized by a plethora of noise resulting from alarms, doors slamming, people talking, employees pushing meal carts, and many other distractions. The main sources of alarms are infusion pumps, mechanical ventilators, intra-aortic balloon pumps, and patient monitors. False alarms, a large number of alarms, and overly loud alarms all contribute to alarm fatigue in medical staff. Alarm fatigue corresponds to reduced response to valid alarms, increased stress levels, hearing loss, and fatigue. In addition, alarm fatigue can cause medical staff to permanently turn off alarms or set their triggering parameters outside of realistic ranges.

Current alarms, due to their frequency and poor positive predictive value (PPV), cause alarm fatigue for clinicians. Alarms in the operating room (OR) sound frequently but in 85-99% of cases do not require clinical intervention. Alarms have a PPV of ~27%, and many 'true' alarms are clinically insignificant. Thus, clinicians distrust alarms, losing confidence in their significance. As alarm frequency increases, clinicians develop 'alarm fatigue' resulting in desensitization, missed alarms, and delayed responses. Alarm fatigue can cause clinicians to set alarm parameters outside effective ranges to decrease alarm occurrence, decrease alarm volumes to inaudible levels, reflexively silence frequently insignificant alarms, and be unable to distinguish alarm urgency. Yet, when a 'true alarm' that requires clinical intervention is ignored or inadvertently missed, patient harm can result. Decreasing the incidence of false alarms will require improvements in sensors and processing algorithms. Even with optimal activation, there will always be false and uninformative alarms (e.g., apnea alarm when the patient is being intubated), the need for reliable response to true alarms signifying actionable situations, as well as the need to reduce noise in clinical settings.

The Occupational Safety and Health Administration (OSHA) has set legal limits on occupational noise exposure—e.g., no more than 8 hours of 90 dB exposure with the exposure time halving for every increase of 5 dB (e.g., ≤4 hours if 95 dB). For reference, a jackhammer at 15 meters yields 95 dB while a vital signs monitor with a QRS volume setting of 2 located 3 feet from an anesthesia provider at the head of the OR bed yields 80 dB. In the OR, the latter noise adds on top of the ventilator, surgical sounds (e.g., orthopedics drill, suction, clanging instruments), intercom, conversations, and other alarms. Since every manufacturer believes that their device's 'emergency condition' is most important, the accumulating sound creates a vicious positive feedback loop that may be detrimental to patient safety and practitioner well-being. As a result, clinicians and patients are subjected to noise levels that far exceed OSHA recommendations.

Being exposed to up to 700 alarms per day in most acute care settings produces alarm fatigue and may precipitate hearing loss. While the World Health Organization recommends that noise levels be <30 dB at night in hospitals, current levels are closer to 60 dB. For healthcare providers, excessive noise causes miscommunication, inattention, loss of concentration, memory impairment, headaches, burnout, fatigue, and impaired task performance. These outcomes not only lead to clinician dissatisfaction but also have negative consequences on their ability to provide high quality patient care.

For ICU patients, excessive noise and alarm fatigue can affect sleep, wound healing, mental state, and immune function that may lead to increased blood pressure, hemodynamic instability, increased sedation requirements, loss of sleep, and delirium. More importantly, noise in the ICU can result in post-traumatic stress disorder (PTSD) for patients.

The Diagnostic and Statistical Manual of Mental Disorders, Fifth Edition (DSM-V), defines PTSD as a potentially debilitating psychiatric condition, which develops as the result of being exposed to a traumatic event or events, and characterizes PTSD by symptoms in three domains: 1) symptoms of re-experiencing such as intrusive thoughts, 2) symptoms of avoidance and emotional numbing, and 3) symptoms of increased arousal. Furthermore, these symptoms must meet two criteria to satisfy the diagnostic criteria: 1) they must cause significant impairment in social, occupational, or other important functional domains, and 2) they must be present for at least one month after exposure to the traumatic event or events. Studies reported in previous literature describe a wide range of PTSD prevalence in the ICU, ranging from 5%-63%. Yet to this date it has never been studied whether noise in the ICU is an independent predictor for PTSD.

There is, however, recent data that demonstrates PTSD symptoms in ICU patients. A study conducted on 382 patients at the BRAIN-ICU at Vanderbilt showed that at 12 months post ICU discharge 7% of patients had PTSD. However, it is important to point out that these patients had a 15% incidence of intrusion, a 43% incidence of avoidance, and a 46% incidence of hyperarousal symptoms; yet unless all three symptoms were present together, a formal PTSD diagnosis could not be made even though having just one of these PTSD symptoms can significantly affect one's quality of life.

Furthermore, there is research to indicate that these symptoms are elicited by noise from alarms. Research shows that patients with delusional memories are more likely to develop PTSD symptoms than patients with factual memories. Periods of delirium with associated delusions may predispose patients to PTSD. On the other hand, periods of alertness, which permit the organization of factual memories, may serve as a protective role and prevent the development of PTSD-related symptoms after discharge. However, periods of alertness cannot occur if the patient has excessive daytime sleepiness from poor sleep in the ICU due to alarm and non-alarm noise.

Alarms that interfere with sleep may also weaken the immune system by decreasing lymphocyte production. The Food & Drug Administration's Maude database contains numerous voluntary reports of alarm-related injuries including 216 deaths over 5 years (2005-10); this likely significantly underestimates the incidence of alarm-related harm.

There is a recent national focus on alarm management and patient safety. The Joint Commission's (TJC) recent attention on alarms exemplifies societal concern about this issue. TJC declared alarm management and safety to be one of their 2014 National Patient Safety Goals. They now require hospitals to prioritize alarm management and to assess the appropriateness and priority of every alarm in their hospital. The Emergency Care Research Institute (ECRI) identified alarm hazards as number one of the "Top 10 Health Technology Hazards" in 2013. They specifically cited turning down alarm volumes to inaudible levels as a major safety issue. The mission of a 2011 Association for the Advancement of Medical Instrumentation (AAMI)-FDA summit on alarms was "by 2017, no patient will be harmed by adverse alarm events."

SUMMARY OF THE INVENTION

Alarms are used in clinical settings to alert medical staff of the status of patient monitoring and treatment devices. In general, an alarm will sound when a parameter for a device exceeds a threshold value. The alarm alerts medical staff to check the status of the device and take appropriate action. A clinical setting is characterized by a collection of background noise sources including alarms, doors slamming, individuals talking, moving carts, etc. Some current alarms are designed to be louder than background noise. However, alarms can contribute to background noise and thereby create a vicious cycle of alarm competition and reduce the salience of individual alarms.

Alarms are needed that will result in both quick and accurate clinical responses, which will in turn limit the noise contribution due to alarms and minimize negative effects on patients. A preliminary study was conducted in an anechoic chamber in which clinicians (n=17) performed a simulated clinical drug administration task in response to alarms of varying signal-to-noise ratios (SNR) relative to hospital background noise at 60 decibels (dB). FIG. 1 shows that clinical performance accuracy increased as the SNR increased. However, there was no accuracy gain from −11 dB SNR to +4 dB SNR. FIG. 2 shows that the inverse efficiency score (IES), which is the response time adjusted by accuracy, also had no performance gain from −11 dB SNR to +4 dB SNR. Therefore, salient multisensory alarms do not need to be louder than background noise.

There are two states to current alarms: volume off (thus unisensory visual) or volume on (multisensory). There is no incumbent, stand-alone technology that monitors noise levels in the ICU in order to modulate the signal output by alarm systems. Current manufactured devices in the ICU contain alarms that try to "out signal" or "out compete" each other with a variety of sound patterns; the general trend is "be louder to be heard."

Embodiments of the invention relate to a dynamic alarm system that can assess the background noise in a clinical environment with sub-minute time sampling and change the alarm output to a desired signal-to-noise (SNR) ratio shown to be below ambient noise (negative SNR) to minimize clinician fatigue and ameliorate deleterious patient outcomes (sleep deprivation, delirium, hypertension, wound healing, etc.), while preserving clinician performance.

A novel feature of an embodiment of the invention includes a monitor to assess background noise and dynamically adjust the psychoacoustic output based on the aural environment.

Embodiments of the invention relate to a patient monitor that includes a dB meter to measure the ambient noise level with time averaging, and adjusts the alarm volume to provide the optimal SNR while ensuring the auditory output is above average human hearing threshold.

Accordingly, embodiments of the invention provide an alarm system configured to automatically adjust an alarm volume based on ambient noise conditions in order to reduce alarm fatigue. Specifically, the dynamic alarm system is capable of adjusting alarm volume without receiving inputs from an alarm system operator. The dynamic alarm system is configured to sense an ambient noise volume and determine an alarm volume based on a signal-to-noise ratio (SNR) wherein the signal is the alarm volume and the noise is the ambient noise volume. The alarm system can be further configured to emit an alarm with a negative SNR wherein the signal is less than the noise (i.e., the alarm volume is quieter than the ambient noise volume).

In particular, one embodiment of the invention provides a method of automatically adjusting an alarm volume based on an SNR wherein the signal is the alarm volume and the noise is the ambient noise volume. The method includes sensing an ambient noise volume of an area around an alarm system. The method also includes determining an alarm volume based on a negative SNR (i.e., the alarm volume is less than the ambient noise volume).

In one embodiment, the invention provides an alarm system that automatically adjusts alarm volume. The alarm system includes a patient monitoring device, a sensor, a controller, and an alarm emitter. The sensor is configured to sense an ambient noise volume of an area around the alarm system. The controller is configured to determine an alarm volume based on a negative SNR (i.e., the signal is less than the noise) wherein the signal is the alarm volume and the noise is the ambient noise volume. The controller is connected to a patient monitoring device and is configured to control the power supplied to the alarm emitter in order to control the alarm volume when the controller receives a triggering signal from the patient monitoring device.

The alarm system can also be configured such that an alarm volume is determined to sound at a positive SNR. An operator can adjust settings of the alarm system to increase or decrease the SNR of an emitted alarm. Additionally, the alarm system is capable of being connected to a patient monitoring device in various configurations. For example, the alarm system can be connected to the patient monitoring device through a wired connection or a wireless connection. Furthermore, the alarm system can be located proximal to a patient monitoring device or in a centralized patient monitoring area where patient data from multiple patient monitoring devices can be monitored.

Embodiments of the invention cure deficiencies of the prior art such that alarm fatigue is reduced without a reduction in the response time or accuracy of clinicians to respond to alarms.

In one embodiment, the invention provides a method of automatically adjusting an alarm volume. The method comprises sensing an ambient noise volume of an area proximal to a device emitting an audible alarm; and determining an alarm volume of the audible alarm emitted from the device based on a ratio of the alarm volume and the ambient noise volume; wherein the ratio of the alarm volume and the ambient noise volume is determined such that the alarm volume is less than the ambient noise volume.

In another embodiment, the invention provides an alarm emitting device comprising at least one controller configured to: sense an ambient noise volume of an area proximal to the alarm emitting device; and determine an alarm volume of the alarm emitting device based on a ratio of the alarm volume and the ambient noise volume; wherein the ratio of the alarm volume and the ambient noise volume is determined such that the alarm volume is less than the ambient noise volume.

Other aspects of the invention will become apparent by consideration of the detailed description and accompanying drawings.

BRIEF DESCRIPTION OF THE DRAWINGS

FIG. 5A graphically illustrates a non-linear least squares analysis performed on voltage to dB calibration.

FIG. 5B graphically illustrates a residual analysis demonstrates a 2 dB resolution.

DETAILED DESCRIPTION

Figure 1:
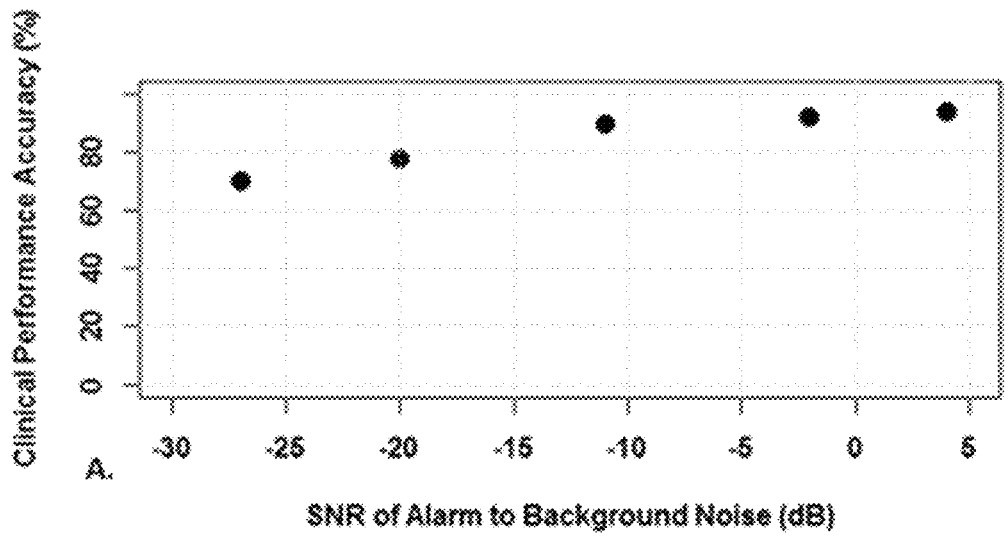
FIG. 1 graphically illustrates clinical performance accuracy results from a preliminary anechoic chamber study.

Before any embodiments of the invention are explained in detail, it is to be understood that the invention is not limited in its application to the details of construction and the arrangement of components set forth in the following description or illustrated in the accompanying drawings. As described in subsequent paragraphs, the specific configurations illustrated in the drawings are intended to exemplify embodiments of the invention and that other alternative configurations are possible. The invention is capable of other embodiments and of being practiced or of being carried out in various ways.

Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected," and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc. It should also be noted that a plurality of hardware and software based devices, as well as a plurality of different structural components may be utilized to implement the invention.

In addition, it should be understood that embodiments of the invention may include hardware, software, and electronic components that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable memory) and executed by an electronic processor to perform specific functionality. As such, it should be noted that a plurality of hardware and software based devices, as well as a plurality of structural components may be used to implement embodiments of the invention.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory.

Figure 3:
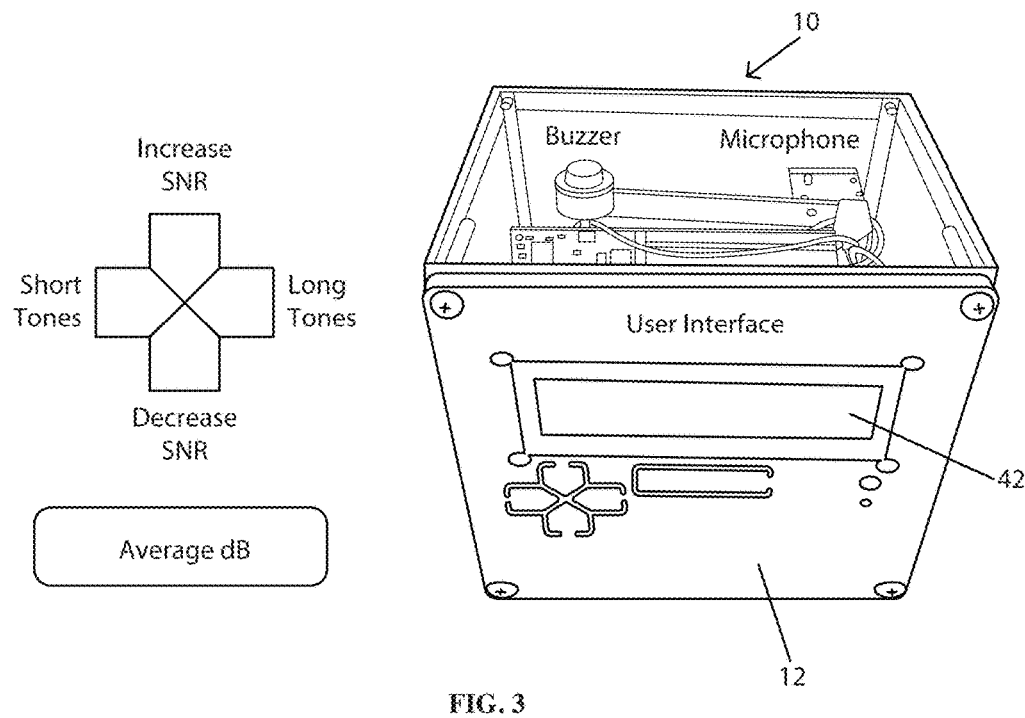
FIG. 3 illustrates a dynamic alarm system according to an embodiment of the invention.

FIG. 3 illustrates an embodiment of a dynamic alarm system 10 that can be incorporated into existing patient monitors and other medical devices. The dynamic alarm system 10 includes a dB meter to measure the ambient noise level with time averaging, and adjusts the alarm volume to provide the optimal SNR while ensuring the auditory output is above average human hearing threshold. One advantage of the dynamic alarm system 10 is that it has both a dB meter and alarm functionalities.

In one embodiment, the dynamic alarm system 10 operates with an input range of 50-90 dB and an output range of 44-81 dB. As illustrated in FIG. 3, the dynamic alarm system 10 is encased in an acrylic case for ease of handling.

Figure 4:
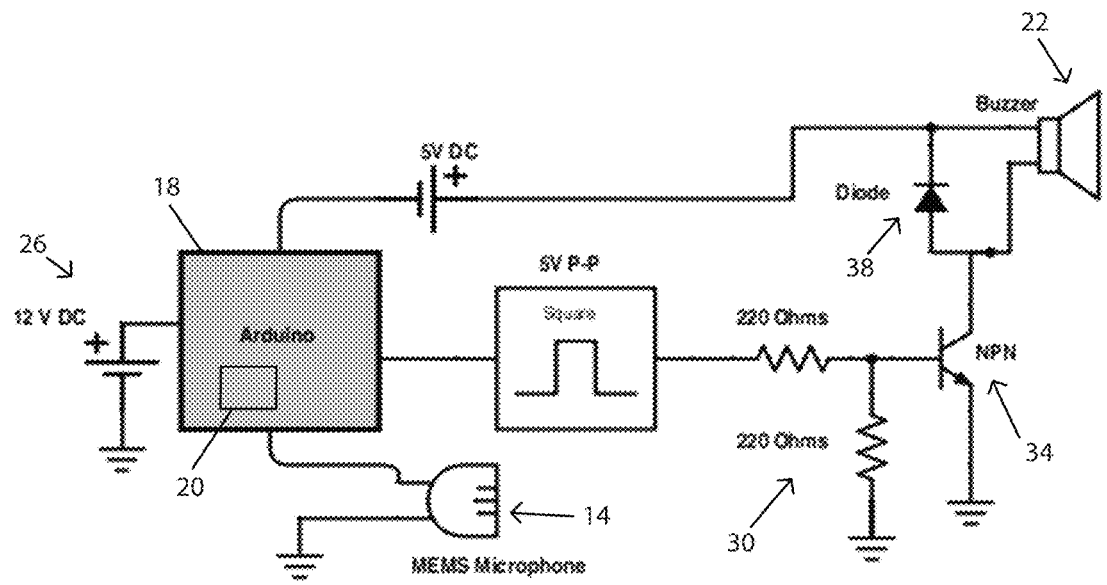
FIG. 4 illustrates a circuit diagram of an embodiment of a dynamic alarm system.

FIG. 4 illustrates an embodiment of a schematic diagram of the dynamic alarm system 10 shown in FIG. 3. The dynamic alarm system 10 includes a housing 12, a microphone 14, an electronic processor 18 (e.g., a microprocessor, application-specific integrated circuit (ASIC), or another suitable electronic device), a non-transitory computer-readable medium 20, a speaker 22, a power adapter 26, a voltage divider circuit 30, a transistor 34, a diode 38, and a display 42. The microphone 14, the electronic processor 18, the speaker 22, the power adapter 26, the voltage divider circuit 30, the transistor 34, the diode 38, and the display 42 communicate over one or more connections or buses.

The computer-readable medium 20 (e.g., read-only memory, random-access memory, or combinations thereof) stores instructions and data. The electronic processor 18 retrieves instructions from the computer-readable medium 20 and executes the instructions to perform a set of functions including the methods described herein.

In particular, the microphone 14 (e.g., ADMP401 MEMs Microphone Breakout Board by SparkFun™) continually senses background noise in the environment. The microphone 14 is connected to an input of the electronic processor 18 (e.g., Arduino UNO R3). The microphone 14 detects acoustic signals and outputs audio signals to the electronic processor 18. The electronic processor 18 reads the audio signals (e.g., background noise) as a dB level in real-time. Based on the background dB level, the speaker 22 (e.g., piezoelectric buzzer) outputs an acoustic signal (i.e., an alarm) of a specific volume to produce a desired SNR.

The microphone 14 reads the audio signal as a voltage. In order to convert this voltage to a dB level, a voltage to dB calibration curve was generated. The calibration curve was built by playing tones of various sound levels for 15 seconds and simultaneously recording the voltage read by the microphone 14 on the electronic processor 18 and the dB level read by a level 2 Amprobe SM-10 sound meter placed next to each other. A total of 50 data points were recorded to create a plot of dB v. Voltage. A non-linear least squares regression analysis was performed to obtain a fit line of the form $dB=(1-e^{-g*V})*(a+b*\ln V)$, demonstrated in FIG. 5A. The electronic processor 18 is programmed to use the equation of this fit line to convert the noise sensed by the microphone 14 to a dB level. A residual plot (FIG. 5B) demonstrates the difference between the observed and predicted dB values. With this fit line, a 2 dB resolution is achieved.

The electronic processor 18 is powered by a 12V DC power adapter 26. One pin of the electronic processor 18, the controlling pin, outputs 5V DC. The electronic processor 18 is programmed so that it causes the controlling pin to be turned on and off at a frequency of 2 kHz (this is the frequency at which the buzzer sounds) such that it produces a 5V, 2 kHz square wave. The output of this controlling pin is connected to a voltage divider 30 such that when it is in its 'on' phase, 2.5V is fed into the base of the NPN transistor 34, and when it is in its 'off' phase, 0V is fed into the base of the NPN transistor 34. The transistor 34 is connected to one side of the speaker 22, which is wired in parallel with a diode 38 to allow the current from the transistor 34 to flow in one direction only. This is necessary because the speaker 22 has effectively unlimited resistance and will not allow the passage of current. When there is current applied to the base of an NPN transistor, the transistor is turned on and current flows to the load connected to it. When there is no current applied to the base of an NPN transistor, the transistor is turned off and no current flows to the load connected to. The other side of the speaker 22 is connected to a different 5V DC output of the electronic processor 18 so that the square wave applied to the transistor 34 controls this 5V DC output's ability to provide voltage to the speaker 22. When the controlling pin of the electronic processor 18 is in the 'off' phase, no current passes through the transistor 34 so no voltage is delivered to the speaker 22 and no sound is produced. When the controlling pin is in the 'on' phase, current passes through the transistor 34 so voltage is applied to the speaker 22 and sound is produced.

Figure 6:
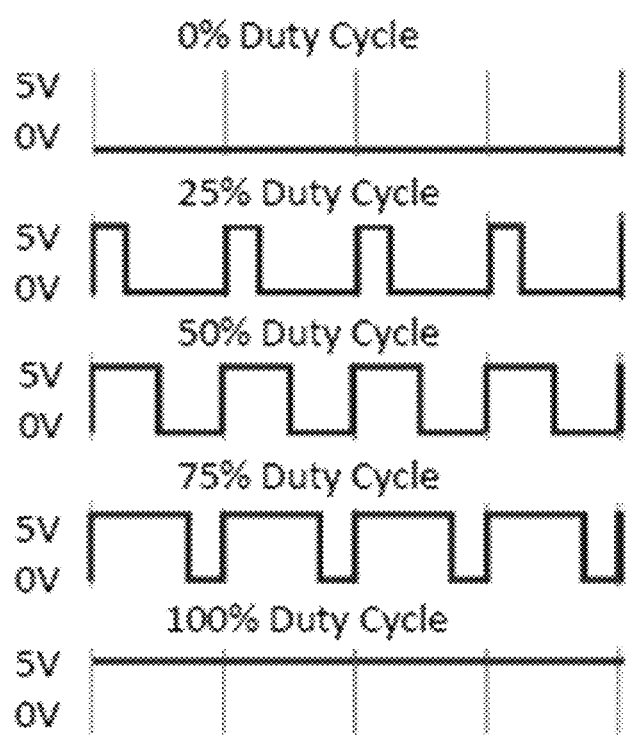
FIG. 6 illustrates duty cycles illustrating an alarms cyclic connection to a power source.

Thus, a 2 kHz, 5V square wave is created to power the speaker 22 by switching the controlling pin between the 'on' and 'off' states. The volume of the speaker 22 is controlled by modulating the duty cycle of this square wave. As illustrated in FIG. 6, the duty cycle characterizes the length of the "on" and "off" states. A duty cycle of 0% represents a flat 0V signal, and a duty cycle of 100% represents a flat 5V signal. Therefore, as the duty cycle of the speaker 22 increases from 0%, the volume of the speaker increases.

In order to calibrate the speaker 22 to produce desired dB levels, the speaker was activated at various duty cycle settings (n=40) and the sound meter was used to record the dB level that each duty cycle corresponds to. The electronic processor 18 was programmed to match duty cycles with dB levels. With this speaker configuration, an alarm output range of 44-81 dB was achieved.

The display 42 (e.g., LCD) is programmed to display the following: 1) a background noise dB reading, 2) an adjustable dB SNR setting, 3) a continuous five second alarm mode, 4) an intermittent 10 second beeping alarm mode, and 5) an average dB reading over time. The dB SNR setting allows the user to choose any positive or negative integer which corresponds to the number of dB above or below the ambient noise level the user wishes the alarm to sound. Once the desired SNR is set, the user can choose to activate one of two alarm modes. One button (right arrow in FIG. 3) produces a continuous 5 second tone based on the chosen SNR, relative to the background dB level when the user pressed the button. Another button (left arrow in FIG. 3) produces 10 half-second tones at the desired SNR, relative to the background dB level read between each alarm tone so that the volume of the tones changes as the background noise changes. The user can press another button (long horizontal button in FIG. 3) to display how long the system has been running and the average dB level over that time.

Figure 7:
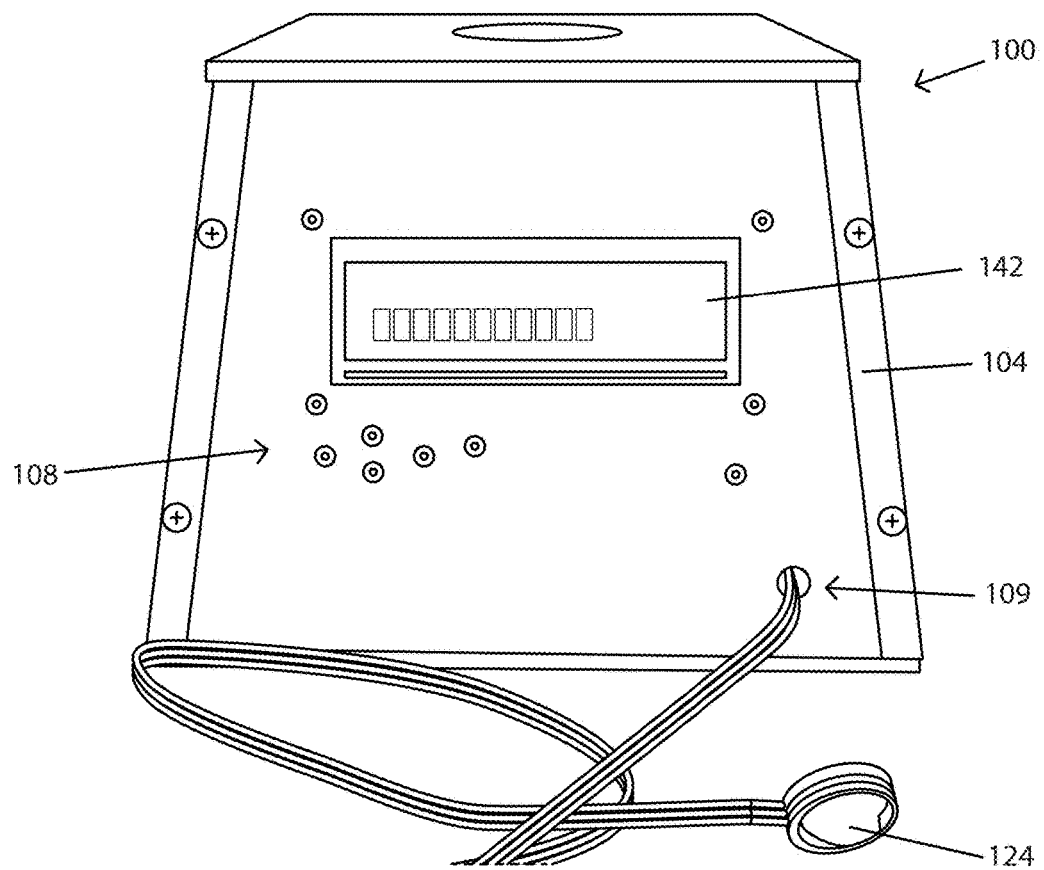
FIG. 7 illustrates a dynamic alarm system according to an embodiment of the invention.

FIG. 7 illustrates a dynamic alarm system 100 according to another embodiment of the invention. The dynamic alarm system 100 can be a standalone system or incorporated into existing patient monitors and other medical devices. The dynamic alarm system 100 includes a dB meter to measure the ambient noise level with time averaging, and adjusts the alarm volume to provide the optimal SNR while ensuring the auditory output is above average human hearing threshold. One advantage of the dynamic alarm system 100 is that it has both a dB meter and alarm functionalities.

As illustrated in FIG. 7, the dynamic alarm system 100 includes a housing 104 and a user interface 108. The user interface 108 (illustrated in FIG. 7 as mechanical buttons) allows a user to provide input to the system 100 on how the system 100 should provide output. For example, the user interface 108 can include such items as a keyboard, a pointing device (e.g., a mouse), buttons on a touch screen, a scroll ball, mechanical buttons, and the like. In some embodiments, output may be audible and/or may be provided within a graphical user interface ("GUI") (e.g., generated by an electronic processor executing instructions and data stored in the memory and presented on a touch screen or other display) that enables a user to interact with the system 100. The dynamic alarm system 100 operates with an input range of 50-90 dB and an output range of 44-81 dB. In other constructions, the dynamic alarm system 100 operates with an output range of 33-81 dB.

As illustrated in FIGS. 13-16, while the output range was designed to encompass 44 to 81 dB, an auditory presentation below 44 dB was tested. FIGS. 13-16 show testing results to 27 dB below background noise at 60 dB. In other words, while the design shows an output range of 44-81 dB (which goes with consistent performance since 11 dB below 60 is 49, and that is within that range), there is still near-threshold of hearing data at 27 dB below 60 dB, or at 33 dB. The 33 dB is a function of the lowest alarm level presented based on the results of the near-threshold of hearing assessment during the experimental paradigm. That is, −27 was used for all participants based on those results, and 27 dB below 60 dB (background noise) is 33 dB.

The dynamic alarm system 100 also includes a port 109 on the housing 104 configured to receive a plug/cable connected to a sensor 124, such as an ECG electrode, a pulse/heart rate sensor, a pulse oximetry sensor, a blood pressure sensor/cuff, temperature sensor, and the like. The sensor 124 is coupled to a patient and detects signals or senses physiological data from contact with the patient.

Figure 8:
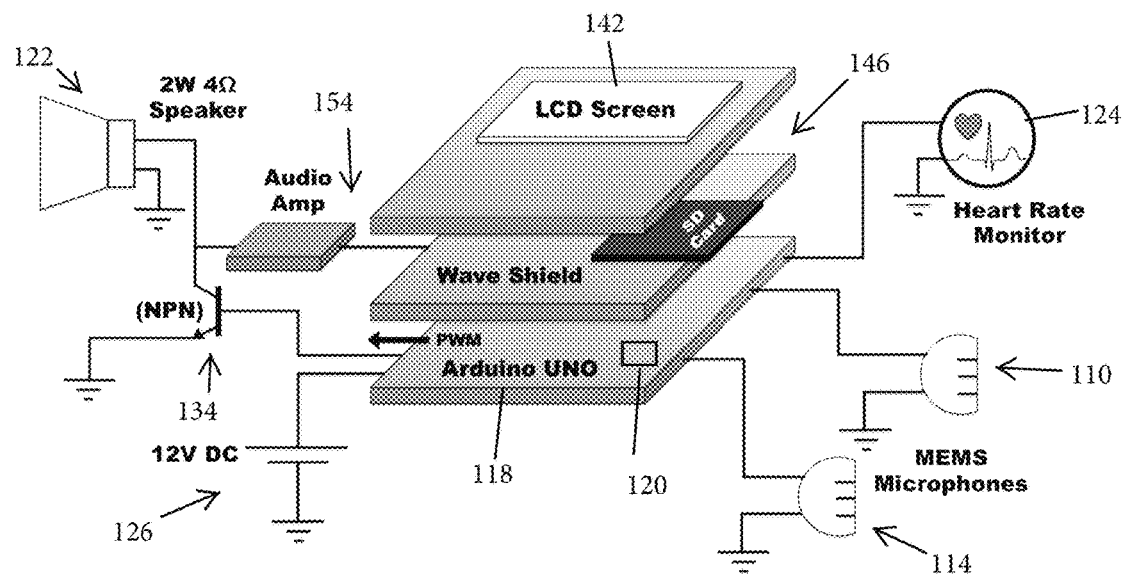
FIG. 8 illustrates a partial schematic of an embodiment of a dynamic alarm system.

FIG. 8 illustrates an embodiment of a schematic diagram of the dynamic alarm system 100 shown in FIG. 7. The dynamic alarm system 100 includes a microphone 110, 114, an electronic processor 118 (e.g., a microprocessor, application-specific integrated circuit (ASIC), or another suitable electronic device), a non-transitory computer-readable medium 120, a speaker 122, a power adapter 126, a voltage divider circuit 130, a transistor 134, a diode 138, and a display 142. The microphones 110, 114, the electronic processor 118, the speaker 122, the power adapter 216, the voltage divider circuit 130, the transistor 134, the diode 138, and the display 412 communicate over one or more connections or buses.

The computer-readable medium 120 (e.g., read-only memory, random-access memory, or combinations thereof) stores instructions and data. The electronic processor 118 retrieves instructions from the computer-readable medium 120 and executes the instructions to perform a set of functions including the methods described herein.

In one embodiment, the first microphone 110 (e.g., ADMP401 MEMs Microphone Breakout Board by SparkFun™) and the second microphone 114 (e.g., ADMP401 MEMs Microphone Breakout Board by SparkFun™) continually sense background noise in the environment. The microphones 110, 114 are connected to an input of the electronic processor 118 (e.g., Arduino Mega 3560 by Arduino™). The microphones 110, 114 detect acoustic signals and outputs audio signals to the electronic processor 118. The electronic processor 118 reads the background noise as a dB level in real-time. Based on the background dB level, the speaker 122 outputs an acoustic signal (i.e., an alarm) of a specific volume to produce a desired SNR. The electronic processor 118 is also electrically connected to the sensor 124 via the port 109 and plug/cable.

Figure 9:
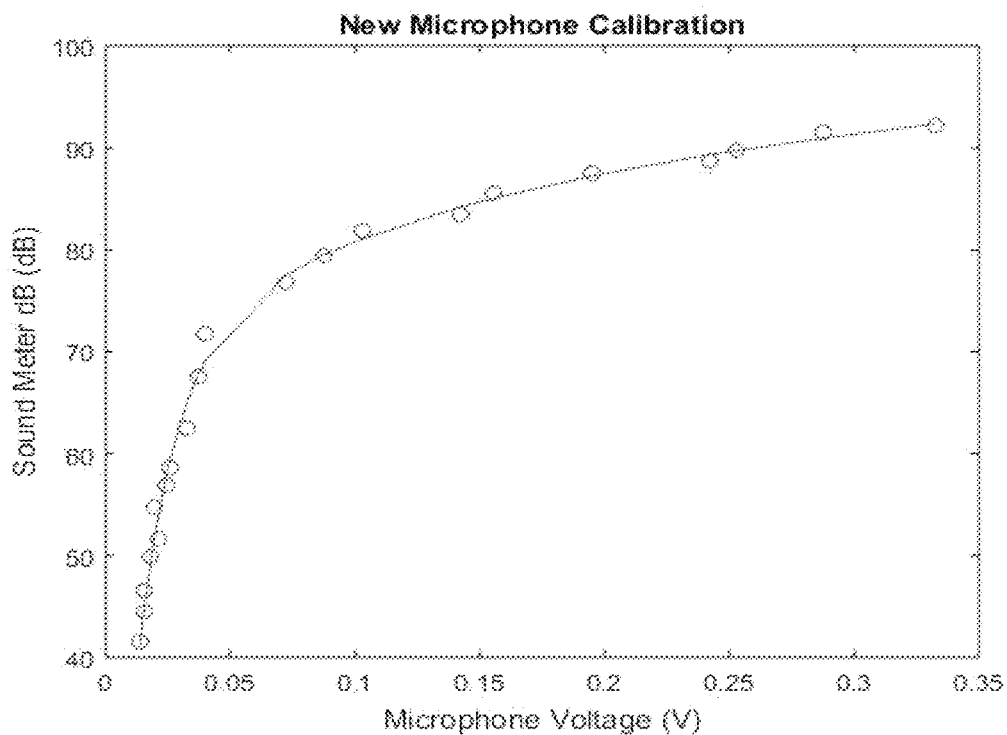
FIG. 9 is a graphical illustration of a microphone calibration curve.
Figure 10:
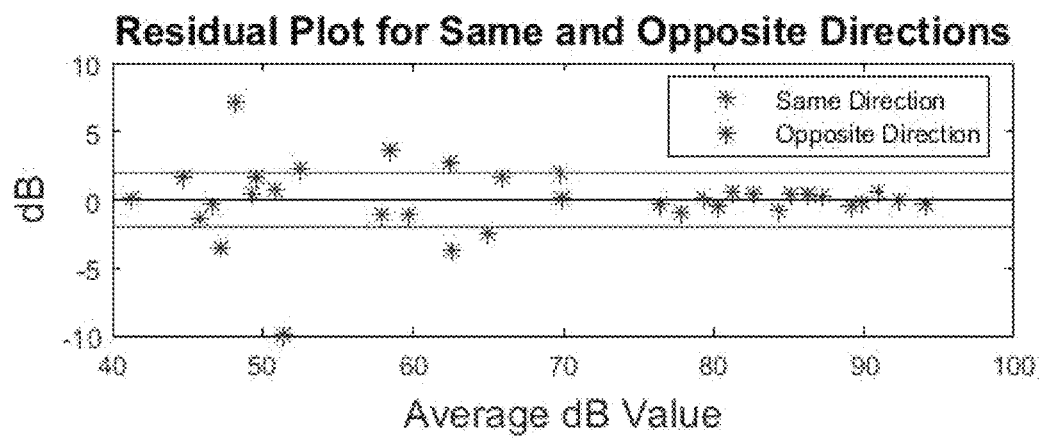
FIG. 10 is a graphical illustration of a dual microphone residuals plot.

The microphones 110, 114 read sound as a voltage. In order to convert this voltage to a dB level, a voltage to dB calibration curve was generated as illustrated in FIG. 9. The calibration curve was built by playing tones of various sound levels for 15 seconds and simultaneously recording the voltage read by the microphones 110, 114 on the electronic processor 118 and the dB level read by a level 2 Amprobe SM-10 sound meter placed next to each other. A total of 50 data points were recorded to create a plot of dB v. Voltage. A non-linear least squares regression analysis was performed to obtain a fit line of the form $dB=(1-e-g*V)*(a+b*\ln V)$, demonstrated in FIG. 9. The electronic processor 118 was programmed to use the equation of this fit line to convert the noise sensed by the microphones 110, 114 to a dB level. A residual plot (FIG. 10) was created to demonstrate the difference between the observed and predicted dB values. With this fit line, a 2 dB resolution was achieved.

With continued reference to FIG. 8, the electronic processor 118 is powered by a 12V DC power supply 126. One pin of the electronic processor 118, the controlling pin, outputs 5V DC. The electronic processor 118 is programmed so that it causes the controlling pin to be turned on and off at a frequency of 2 kHz (this is the frequency at which the speaker 122 outputs sounds) such that it produces a 5V, 2 kHz square wave. The output of this controlling pin is connected to a voltage divider such that when it is in its 'on' phase, 2.5V is fed into the base of the NPN transistor 134, and when it is in its 'off' phase, 0V is fed into the base of the NPN transistor 134. The transistor 134 is connected to one side of the speaker 122, which is wired in parallel with a diode to allow the current from the transistor 134 to flow in one direction only. This is necessary because the speaker 122 has effectively unlimited resistance and will not allow the passage of current. When there is current applied to the base of an NPN transistor 134, the transistor is turned on and current flows to the load connected to it. When there is no current applied to the base of an NPN transistor, the transistor is turned off and no current flows to the load connected to it. The other side of the speaker 122 is connected to a different 5V DC output of the electronic processor 118 so that the square wave applied to the transistor 134 controls this 5V DC output's ability to provide voltage to the speaker 122. When the controlling pin of the electronic processor 118 is in the 'off' phase, no current passes through the transistor 134 so no voltage is delivered to the speaker 122 and no sound is produced. When the controlling pin is in the 'on' phase, current passes through the transistor 134 so voltage is applied to the speaker 122 and sound is produced.

Thus, a 2 kHz, 5V square wave is created to power the speaker 122 by switching the controlling pin between the 'on' and 'off' states. The volume of the speaker 122 is controlled by modulating the duty cycle of this square wave. As illustrated in FIG. 6, the duty cycle characterizes the length of the "on" and "off" states. A duty cycle of 0% represents a flat 0V signal, and a duty cycle of 100% represents a flat 5V signal. Therefore, as the duty cycle of the speaker 122 increases from 0%, the volume of the speaker increases.

In order to calibrate the speaker 122 to produce desired dB levels, the speaker was activated at various duty cycle settings (n=40) and the sound meter was used to record the dB level that each duty cycle corresponds to. The electronic processor 118 was programmed to match duty cycles with dB levels. With this speaker configuration, an alarm output range of 44-81 dB was achieved.

Additionally, as illustrated in FIG. 8, the dynamic alarm system 100 includes a wave shield 146 (e.g., Wave Shield for Arduino Kit [v1.1] by Adafruit™), a digital potentiometer 150 (Digital Potentiometer-10K COM-10613 by Spark- Fun™), and an audio amplifier 154 (e.g., Mono Audio Amp Breakout Board-TPA2005D1by SparkFun™). The wave shield 146 and associated microSD (8 GB Class 10 SD/MicroSD Memory Card by Sandisk) were integrated into the circuitry to enable audio files, that possessed the conventional and novel alarm sounds, to be played on the system 100. The audio amplifier 154 is electrically connected between the wave shield 146 and the speaker 122. The audio amplifier 154 is configured to increase the output alarm volume range and to allow volume control using the digital potentiometer 150.

Figure 18:
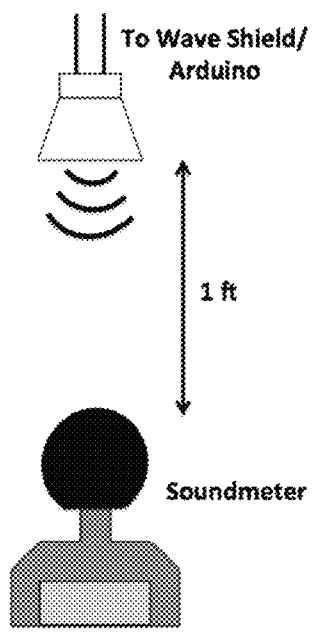
FIG. 18 is a schematic illustration of an experimental volume calibration set up involving placing a sound meter approximately 1 foot away from the loud speaker.
Figure 19:
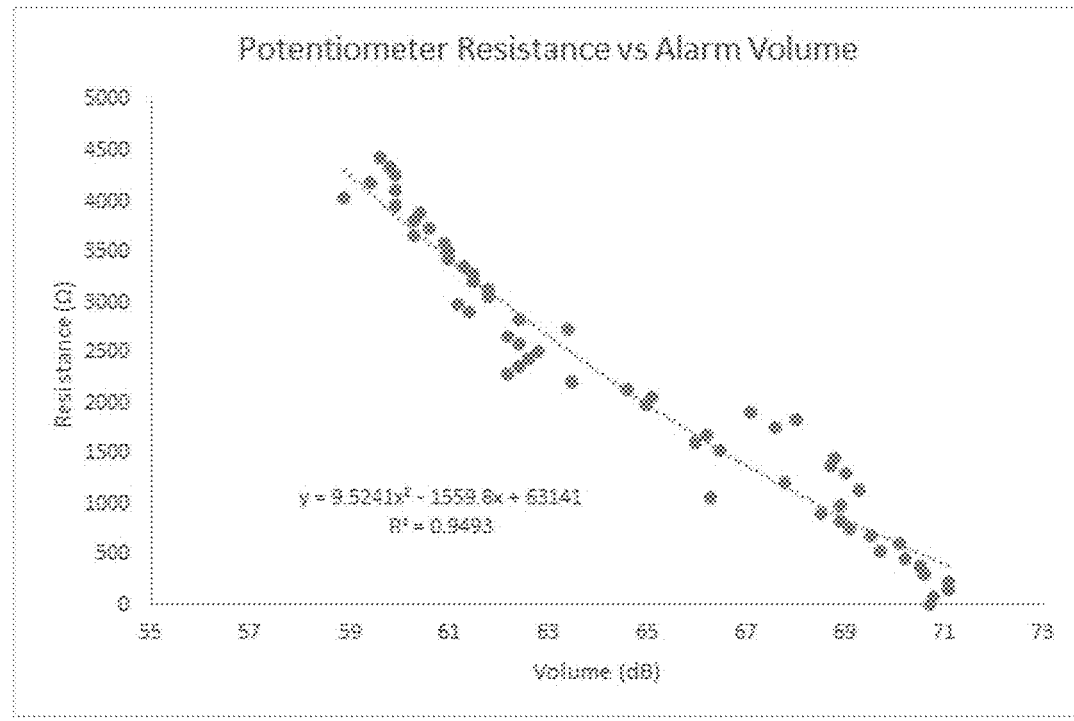
FIG. 19 is a graphical illustration of potentiometer resistance for different alarm volumes.

In order to determine the volume range of the speaker 122 and to calibrate the digital potentiometer 150, an experiment (see FIG. 18) was carried out to measure alarm volume using a sound-meter placed approximately 1 ft from the speaker 122. The dB value was measured for each volume increment. Using an equation from the digital potentiometer data sheet, the step resistance of each increment was calculated. The obtained data were fitted to a polynomial curve in order to create the Arduino code that would allow the user to select the SNR. See FIG. 19.

Figure 20:
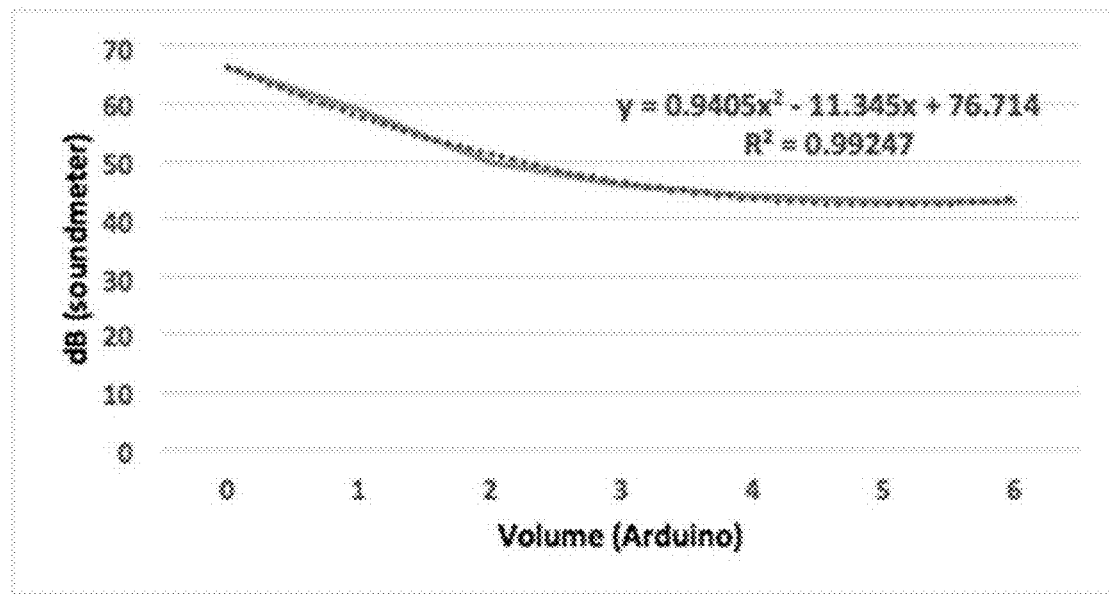
FIG. 20 is a graphical illustration of a calibration that was carried out to test the speaker volume range.

For validation of the volume range of the speaker 122, once incorporated into the device, a similar experimental setup was implemented as illustrated in FIG. 1. The dB values were measured for each volume increment and the data were fitted to a polynomial curve that gave an $R^2$ value of 0.99 (FIG. 20). An alarm volume range of 42.8 dB to 72 dB was derived using this methodology. The average change in alarm volume per software volume setting being 6.67 dB while using the conventional alarm file. This method demonstrated the ability of the system 100 to provide dynamic control.

Figure 11:
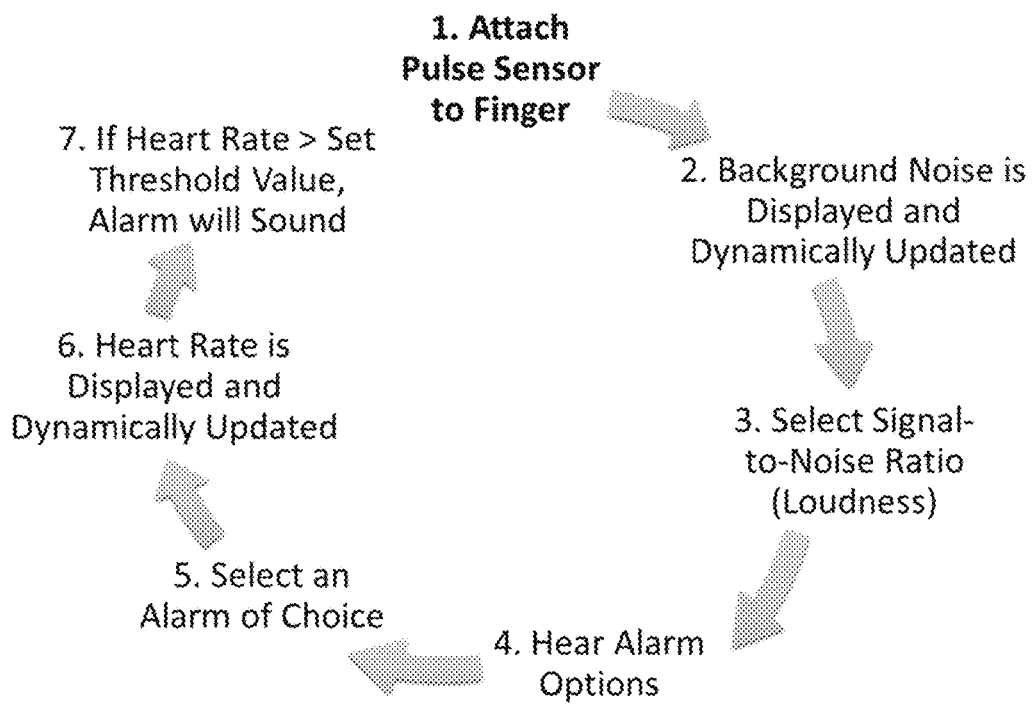
FIG. 11 is a flow chart of a method of operation of a dynamic alarm system.

FIG. 11 illustrates a flow chart of a method of operation of the dynamic alarm system 100 according to an embodiment. As illustrated, a medical device, such as a pulse sensor is applied to a patient's finger and connected to the port 109 on the housing. The system 100 is turned on, and at step 2, the display 142 displays and dynamically updates a reading of the background noise of the environment. The display 142 is programmed to display (but is not limited to) the following: 1) a background noise dB reading, 2) an adjustable dB SNR setting, 3) a continuous five second alarm mode, 4) an intermittent 10 second beeping alarm mode, 5) an average dB reading over time, and 6) a physiological parameter measurement (e.g., a heart rate measurement). At step 3 in FIG. 11, the user selects a desirable SNR for the alarm. The dB SNR setting allows the user to choose any positive or negative integer which corresponds to the number of dB above or below the ambient noise level the user wishes the alarm to sound. Once the desired SNR is set, the user can choose to activate one of two alarm modes. At step 4, in FIG. 11, the user is able to activate and hear the available alarm options, and in step 5 select the desirable alarm option. One button on the user interface 108 produces a continuous 5 second tone based on the chosen SNR, relative to the background dB level when the user presses the button. Another button on the user interface 108 produces 10 half-second tones at the desired SNR, relative to the background dB level read between each alarm tone so that the volume of the tones changes as the background noise changes. Other types of alarm tones are also contemplated. In step 6, the patient data is displayed and if the data exceeds a threshold value, then an alarm will sound in accordance with the user settings (e.g., the selected SNR) of the system 100. The user may also set an upper threshold and a lower threshold at which the alarm is activated. For example, a sensor measurement of the patient's heart rate that is below the lower threshold may indicate bradycardia thereby activating the alarm or a sensor measurement that is above the upper threshold may indicate tachycardia thereby activating the alarm. Additionally, the user can press another button on the user interface 108 to display how long the system has been running and the average dB level over that time.

Below is an embodiment of a portion of the software code used to program the electronic processor 18 and 118:

```
while (milis( ) - startMillis < sampleWindow)
{
    sample = analogRead(A1);
    inp=analogRead(0);
    if(inp>140 && inp<150)
    {
        diff++;
        lcd.begin(16,2);
        lcd.print(lasttotal);
        lcd.print("decibels");
        lcd.setCursor(0, 2);
        lcd.print("Volume: ");
        lcd.print(diff);
        delay(500);
    }
    if(inp==329)
    {
        diff--;
        lcd.begin(16,2);
        lcd.print(lasttotal);
        lcd.print("decibels");
        lcd.setCursor(0, 2);
        lcd.print("Volume: ");
        lcd.print(diff);
        delay(500);
    }
    If(inp==0)
    {
```

In particular, this software code 1) checks the ambient decibel level, 2) checks to see if the dB offset has been adjusted by the user and updates the display, and 3) checks to see if the alarm has been activated by the user. If so, an alarm is triggered to sound at a specified dB offset for a desired period of time.

As noted above, several objectives of an embodiment of the invention are to improve hospital rooms (e.g., operating room (OR)) alarm design, improve clinician performance, and minimize alarm fatigue. A premise of embodiments of the invention is that better use of audible and visual signals will facilitate responses to alarms. A new experimental paradigm based on combined use of visual and audible information is developed and validated. National entities have identified alarms as a top health technology hazard due to failure of staff to respond to valid alarm conditions in a timely manner or to take appropriate action in response to the alarm. Yet, false alarms, too many alarms, and overly loud audible alarms all contribute to alarm fatigue that reduces response to valid alarms (i.e., "cry wolf" syndrome), worsens clinicians' stress, hearing loss, and fatigue, and can adversely affect patients' sleep, wound healing, mental state, and immune function. Current alarms are designed to be louder than background noise. However, multiple alarms raise the background noise thereby creating a vicious cycle of alarm competition and reducing the salience of individual alarms. In well-established neuroscience literature, behavioral facilitation can actually be greater when multisensory (i.e., auditory and visual) targets are embedded in noise, such as the gains that are achieved by watching the mouth movements of a speaker in a noisy room. Several proof-of-concept pilot studies support this finding. Further, both response time and accuracy improve with the combined use of auditory and visual (i.e., multisensory) stimuli. In this project, a unique experimental model is employed to study, in a rigorous empirical manner, the effects of integrated auditory and visual alarm design on clinician detection and decision-making.

Specific Aim 1: To determine the stimulus-response (S-R) relationship between alarm sound level and performance in clinical decompensation events of varying complexity, while concurrently attending to a distracting audiovisual (AV) secondary task. Participants' near-threshold auditory perception of alarms and performance (response time (RT) and accuracy) for selection of the correct therapeutic intervention will be measured and the S-R curve shift will be analyzed across complexity of clinical events.

Hypothesis 1A: The dynamic auditory alarm range (encompassing 90% of the overall change in response time and accuracy) will be between −20 and −10 dB below ambient OR noise at 60 dB.

Hypothesis 1B: Efficiency (RT/Accuracy) will be equivalent across clinical complexities at negative signal-to-noise ratios (SNRs) because non-fatiguing alarms will not hinder clinical decision-making.

In Experiment 1, a novel experimental paradigm was used to present alarms during simple and difficult clinical scenarios to determine the S-R relationships for changes in auditory alarm intensity, spanning negative to positive SNRs, while performing an AV secondary task designed to tax attentional and decisional resources. The result was an S-R curve in dB above ambient noise.

Specific Aim 2: To determine the most salient psychoacoustic alarm qualities (pitch, direction, timbre) within the dynamic range found in Experiment 1 that improves performance and ascertain how these qualities interact with visual factors (centrally versus peripherally presented visual alarms).

Hypothesis 2A: The largest performance gain will be with alarms that are informative (pitch direction concordant with vital sign direction, interval difference, and rhythm) and that correlate with clinical status.

Hypothesis 2B: Novel auditory alarms will be more salient when visual alarms are presented in the peripheral versus the central visual field since a weakened visual stimulus (common in clinical settings) will afford multisensory enhancement.

Experiment 2 will employ Experiment 1's paradigm to study novel alarm sounds and integrate audible and visual cues to create an effective multisensory alarm.

Preliminary Studies

Multisensory input leads to facilitation and improved response time and accuracy. Dr. Wallace, amongst many other neuroscience labs, has shown that integration of information across multiple senses (i.e., audition and vision) improves detection, accuracy, and response time. Multisensory integration can be modulated by attention and sensory training protocols enhance performance. A significant foundation of psychological, neuroscience, and human factors research has informed applied studies to examine how divided attention abilities might be improved. For example, training focused on the combined use of visual and auditory (multisensory) cues has been shown to significantly increase sensory performance and perception.

Multisensory training can improve attentional load processing and performance on pulse oximetry tasks. An anesthesiologist must remain vigilant in an environment rife with multisensory information. The relevant data must be discerned and assimilated while irrelevant data disregarded. Dividing attention and triaging events is imperative, and this challenge is worse when attentional resources are at or beyond capacity. Dr. Schlesinger, working in Dr. Wallace's lab, found a substantial (17%) performance decrement in clinicians' aural perception of subtle changes in pulse oximetry in an attentionally demanding environment with OR background noise. Increasing degrees of visual attentional load resulted in deficits in both response time and accuracy to detect a change in oxygen saturation. Using the same paradigm, only 2 hours of multisensory perceptual training over a 2-day period helped anesthesiologists improve in absolute clinical accuracy and in relative response time in a noisy OR environment during high attentional load conditions. Given that auditory response times are in the hundreds of milliseconds range, subsecond performance improvement confers a dramatic difference. These pilot data demonstrate that optimal multisensory stimuli can improve clinicians' response during patient monitoring.

Figure 2:
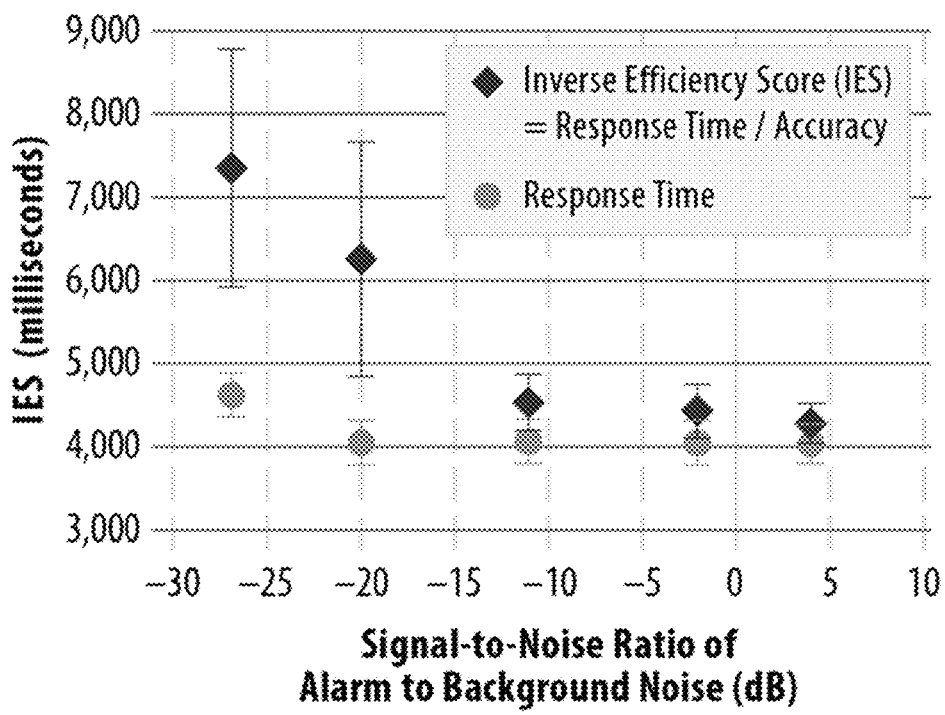
FIG. 2 graphically illustrates efficiency of clinician response to all clinical scenarios with varying alarm SNR.

Novel experimental paradigm: the experimental paradigm was fully developed for delivering different alarm sounds to clinicians in an anechoic chamber in a realistically simulated OR sound environment. Pilot data (n=17 attending anesthesiologists) from Experiment 1 and Hypothesis 1B, supports the hypotheses that clinician performance/efficiency to alarms at −11 dB below ambient OR noise levels is similar to the same alarm sounds at +4 dB (FIG. 2).

Experimental Design and Methods

Study Population: Anesthesiology resident physicians were recruited by electronic mail to attain 30 participants for each of the two experiments. Participants may complete both experiments.

Measurements. The independent variables were: alarm volume (dB above ambient OR background noise) (Aim 1), clinical complexity (Aim 1), monitor location (Aim 2), and alarm psychoacoustic qualities (Aim 2). The dependent variables were: response time for a therapeutic choice (milliseconds), accuracy of audiovisual distracting task (to ensure attention is divided amongst all tasks), and therapeutic choice accuracy (percent correct).

Figure 17:
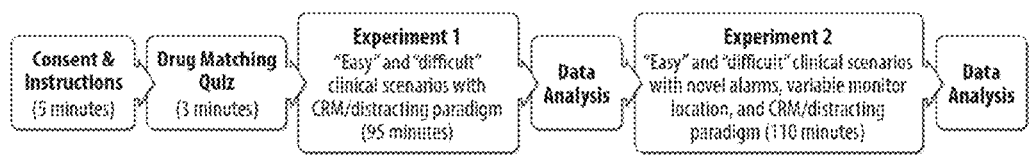
FIG. 17 illustrates the experimental paradigm developed for delivering different alarm sounds to clinicians in an anechoic chamber in a realistically simulated OR sound environment.

Paradigm Methods are illustrated in FIG. 17.

Pre-study assessment: After written consent, participants were presented a list of 8 drugs. The participants completed a matching test to ensure that they are familiar with each drug's indications.

Primary task—Auditory Stimulus and Visual Display: The primary task included two "easy" scenarios: isolated tachycardia (correct intervention: esmolol) and isolated bradycardia (correct intervention: atropine); and two different "difficult" clinical scenarios: hypotension and bradycardia (correct intervention: ephedrine) and hypotension and tachycardia (correct intervention: phenylephrine). The auditory alarm stimulus mimicked the high priority tone on the Philips© MP70 patient monitor (Philips Medical, Andover, Mass., USA). The amplitude was varied, but matched the pitch (frequency=1050 Hz) and the timing of the alarm (sounds every 1.05 sec.). The monitor will be a 4 quadrant "big numbers" profile without waveforms.

Experimental Setting: Fieldwork in the OR presents difficulties in controlling for confounding variables. All of our experiments will be performed in an anechoic chamber to allow for precise control over alarm and noise level. The anechoic chamber is ideal for conducting experiments on alarms and monitoring because it is a quiet, controlled acoustic setting enabling the presentation of multiple precise auditory signals.

Secondary Tasks to Adjust Attentional Load. Auditory Task: The Coordinate Response Measure (CRM) is a validated speech paradigm consisting of three different male talkers and 256 unique sentences per talker. The construction of each sentence follows the formula, "Ready [call-sign], go to [color]-[number], now." As multiple sentences are presented simultaneously, the auditory system struggles to isolate a single talker. Such effortful listening is ideal for this project because the participant must devote considerable attention to this task and it mimics clinical situations in which there are competing talkers. Visual Task: The participant must respond via key press when a yellow LED light becomes non-illuminated. This is a non-alerting visual attention task that thematically simulates focused attention (e.g., on the surgical field or monitor).

Experiment 1: Hypothesis 1A: The dynamic auditory alarm range (encompassing 90% of the overall change in response time and accuracy) will be between −20 and −10 dB below ambient OR noise at 60 dB. Hypothesis 1B: Efficiency (RT/Accuracy) will be equivalent across clinical complexities at negative SNRs. Pilot data has informed our methodology. For each participant, we will first determine their near-threshold hearing by using a 7-min. 3 down 1 up staircase function with 8 reversals. The primary/clinical task will utilize two "easy" and two "difficult" clinical scenarios. Accuracy will be based on the correct medication selections for each clinical scenario with demerit for abandonment of the secondary task. To generate an individual amplitude-response curve, each participant will spend about 67 minutes responding to five 13.3-min. blocks containing five different randomly allocated alarm volumes (near-threshold, −20 dB, −11 dB, −2 dB, and +4 dB from 60 dB OR background noise) for a total of 20 trials at each alarm level and clinical event type (easy and difficult). A 5-min. break will be offered after every block. Throughout, the participant will hear actual OR background noise that does not incorporate other alarms or monitor beeping, and will perform the CRM and visual tasks to assure a sufficient attentionally demanding load. Total contact time will average 103 minutes.

Experiment 2: Hypothesis 2A: The largest performance gain will be with alarms that are informative and correlate with clinical status. Hypothesis 2B: Novel auditory alarms will be more salient when visual alarms are presented in the peripheral visual field. Starting with the same paradigm and scenarios described in Experiment 1, each of the 30 (crossover allowed) participants will spend ~80 minutes responding to six 13.3-min. trials with the three alarm volumes found in Experiment 1 to cover the dynamic performance range, an equal number of traditional versus novel alarms, and two different visual monitor locations (0° and 45° off forward). A 5-min. break will be offered after every block. We anticipate that the novel tachycardia alarm will be a 1-sec. duration, major-$7^{th}$ intervallic sweep, ascending from 1050 Hz ($C^6$) (red alarm) to 1982 Hz ($B^6$). The novel bradycardia alarm will be a 1-sec. duration, major-7th intervallic sweep, descending from 1050 Hz to 556 Hz ($C^{\#5}$). The novel hypotension alarm will be a 1-sec. duration, major-$7^{th}$ intervallic pattern, descending from 1050 Hz (one ¼ note over 500 ms) to 556 Hz (two ⅛ notes over 500 ms). Total contact time will average 110 minutes.

Statistical Analysis

Power Analysis: Based on our pilot data from experiment one, we calculated that 30 participants are needed to detect a difference of 1000 ms with 95% power. Therefore, with two covariates, we plan to study 30 participants in each experiment.

Figure 12:
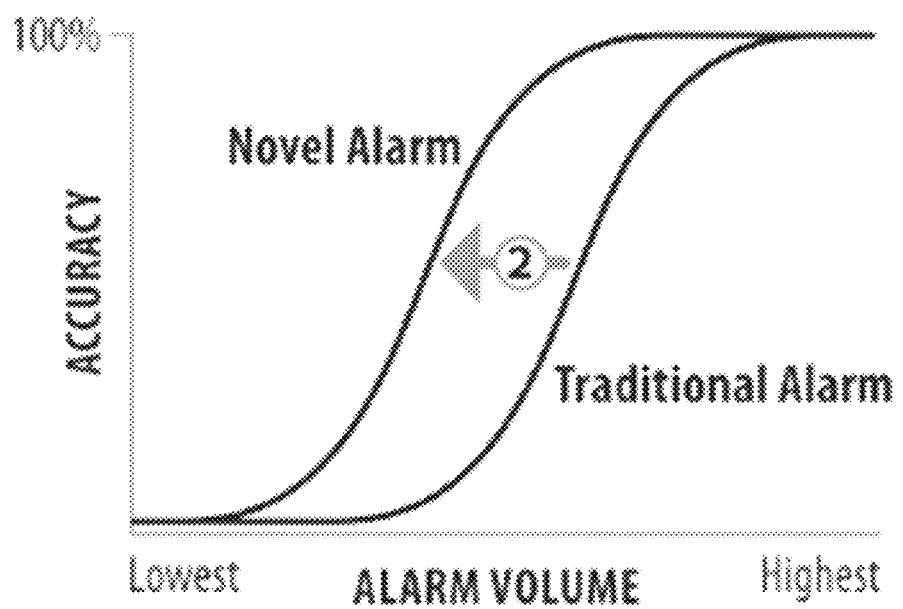
FIG. 12 depicts the novel alarm's predicted effects.

Data Analysis and Interpretation: Data from each individual will be captured and analyzed using MATLAB® (MathWorks). The proposed experiments will generate psychometric data that can be modeled as a sigmoid function (FIGS. 2 and 12). In these figures, we show actual stimulus (alarm volume)—response (response time/accuracy) (Experiment 1) and example type of alarm (Experiment 2). Aggregate average curves for multiple participants would also show 95% confidence intervals. $ED_{50}$'s can be calculated and compared.

Aim 1: Nonlinear mixed effects regression will be used to estimate the symmetric stimulus boundaries (denoted $ES_5$ and $ES_{95}$) that include 90% of the dynamic range in response time. The S-R relationship will be modeled using a four- or five-parameter logistic curve. The five-parameter curve will be used if there is evidence of asymmetry in the S-R relationship. Each logistic curve parameter will have a random effect indexed by participant. This approach simultaneously accounts for between-participant heterogeneity in the S-R relationship, and within-participant correlation among repeated measurements. The $ES_5$ and $ES_{95}$ will be summarized using a point estimate and 95% confidence interval.

Aim 2: Response times and accuracy will be evaluated using linear and generalized linear mixed effects models, respectively, adjusting for scenario difficulty ("easy" vs. "difficult"), and alarm volume. The within-participant correlation in response time and accuracy measurements will be accommodated using a random intercept indexed by participant. The conditional effects of each adjustment factor on mean response time and accuracy, and the relevant contrasts will be summarized using 95% confidence intervals. Intervals that fail to cover the appropriate null value will be considered statistically significant.

Figure 13:
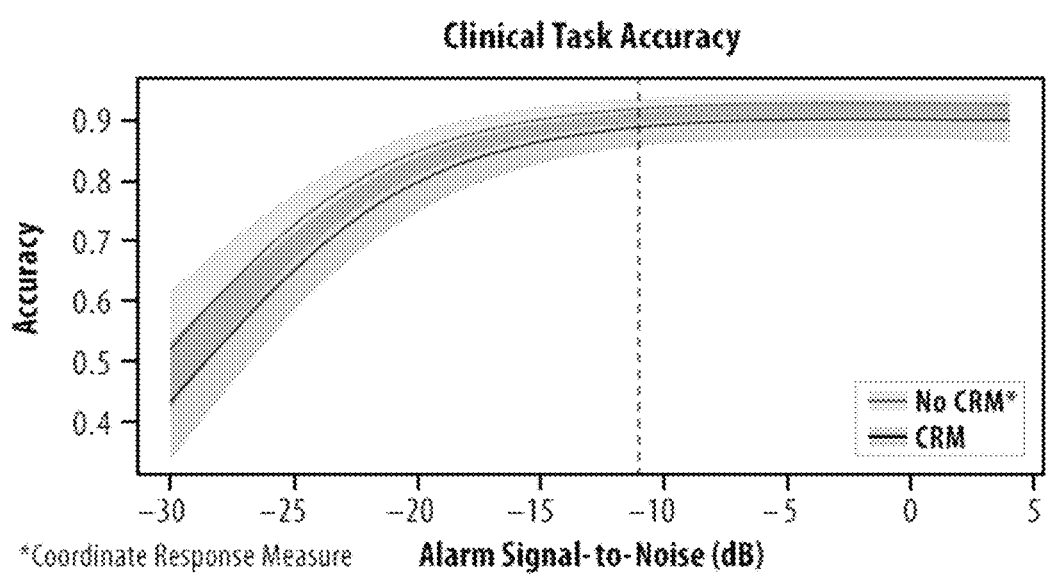
FIG. 13 is a graphical illustration of clinical task accuracy.
Figure 14:
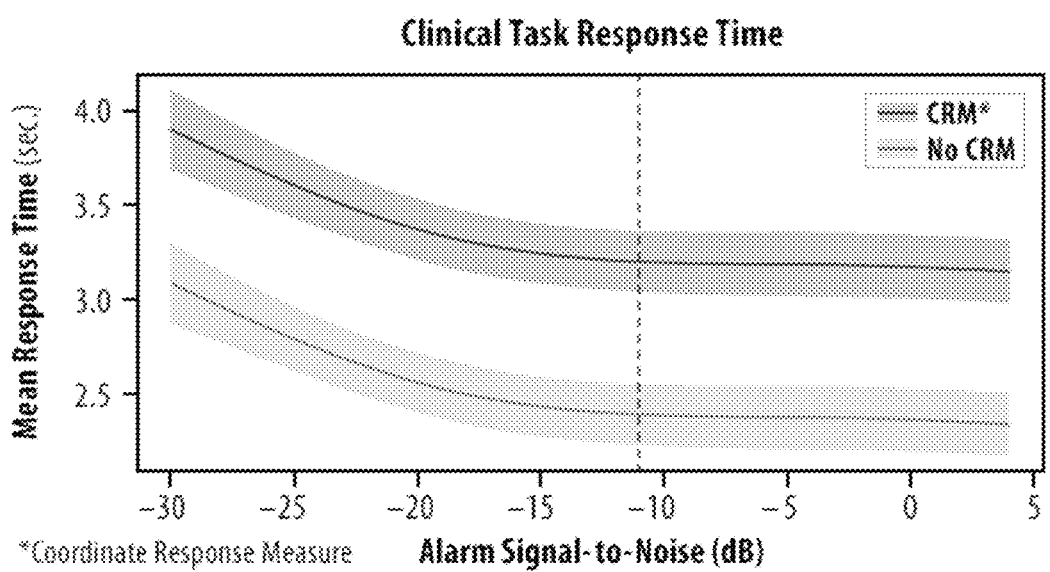
FIG. 14 is a graphical illustration of clinical task response time.

Based on the staircase function to ascertain participants' near-threshold of hearing discussed above, all participants were within 1 dB of each other from −27 to −28 dB below background noise at 60 dB. Thus, the lowest/softest alarm presentation was at −27 dB below background noise at 60 dB, equating to 33 dB. Anechoic laboratory data was collected and analyzed. FIGS. 13 and 14 illustrate the results of mixed-effects logistic and linear regression, adjusting for alarm signal-to-noise ratio (three knot natural spline), and the concurrence of either a CRM or vigilance task (True/False). The three independent variables were assessed for pairwise interactions. However, there was no significant evidence of interactions (using a likelihood ratio test), and thus the interaction terms were omitted. A random intercept, indexed by participant, was used to account for correlation among responses arising from the same session and participant. The bands in the figures are pointwise 95% confidence bands that were generated using a parametric bootstrap method. The associations between alarm signal-to-noise ratio and each outcome (likelihood that emergency was addressed, addressed correctly, and the response time) were all statistically significant (Wald-test p-value <0.001 for each outcome). For each outcome, concurrence of the CRM task was significantly associated with poorer performance (even though the corresponding confidence bands may overlap). Specifically, the odds of correctly addressing the clinical task were smaller by 30% (95% CI: 18, 39) when there was a concurrent CRM task. Similarly, response time was larger by 0.81 s (95% CI: 0.76, 0.87), on average. There was no significant evidence that concurrence of the vigilance task impacted any of the clinical task outcomes. The figures do not depict the raw data, but rather the model-fitted values.

Figure 15:
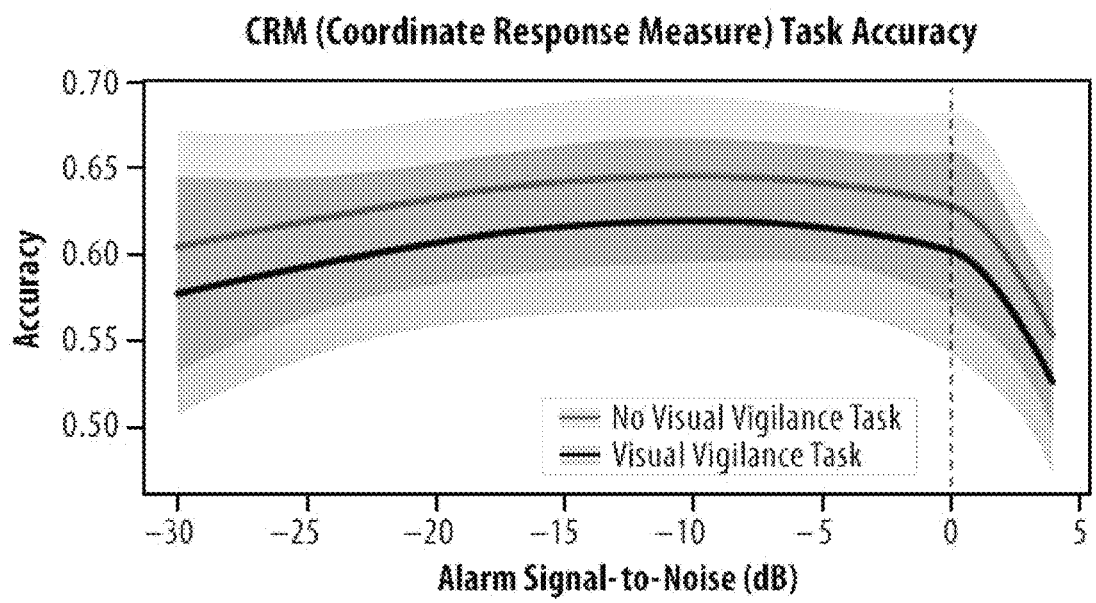
FIG. 15 is a graphical illustration of Coordinate Response Measure (CRM) task accuracy.
Figure 16:
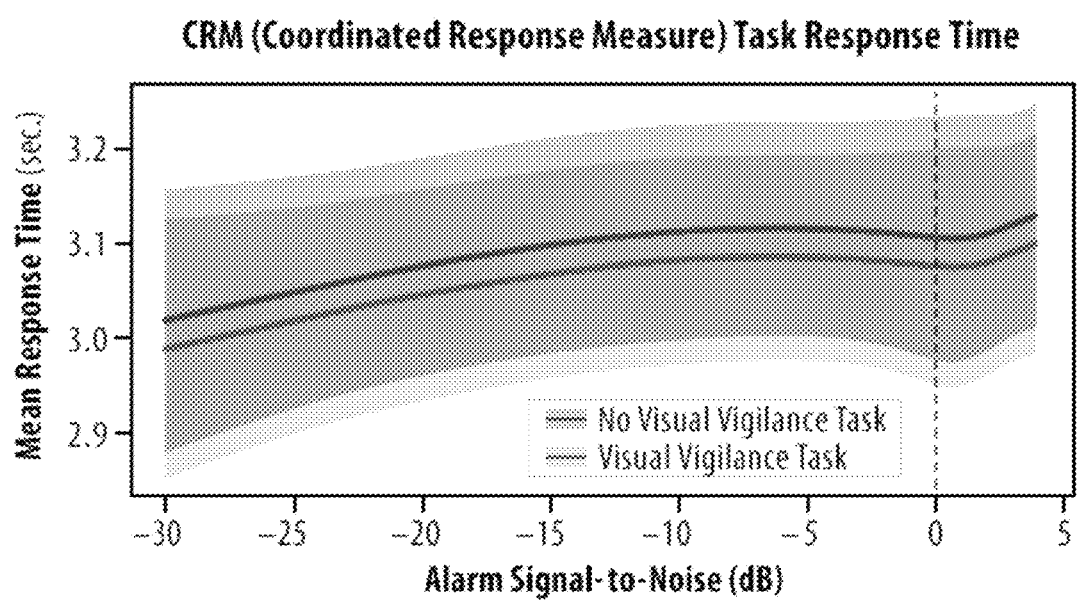
FIG. 16 is a graphical illustration of CRM task response time.

FIGS. 15 and 16 illustrate the results of mixed-effects logistic and linear regression, adjusting for the concurrence of an unaddressed clinical task (with alarm), alarm signal-to-noise ratio (three knot natural spline), and concurrence of a vigilance task (True/False). The likelihood of addressing the CRM task (either correctly or incorrectly) was significantly less when there was a concurrent clinical task (OR: 0.68; 95% CI: 0.57, 0.80) or vigilance task (OR: 0.58; 95% CI: 0.49, 0.70). There was no evidence of an interaction between the effects of the clinical and vigilance tasks (p=0.475). Nor was there evidence (p=0.600) of an effect of alarm volume on the likelihood of addressing the CRM task.

However, there was significant evidence that alarm level affects the likelihood of correctly addressing the CRM task (p<0.001) and response time (p=0.031). Specifically, alarm level had little effect on the odds of correctly addressing the CRM task for negative SNR, but was associated with a drop in the odds for positive SNR. Alarm level was positively correlated with response time across all alarm levels. In addition, when there was a co-occurring unaddressed vigilance task, the odds of correctly addressing the CRM task were further reduced by 10% (OR: 0.90; 95% CI: 0.82, 0.98). In contrast, adjusting for the effect of co-occurring clinical task, the co-occurrence of a vigilance task was associated with slightly shorter (but statistically significant) response time (0.03 s; 95% CI: 0.00, 0.06; p=0.033). There was no evidence of an interaction between co-occurring vigilance and clinical tasks in their effects on response time.

The present disclosure described herein and representative embodiments, are exemplary, and are not intended as limitations on the scope of the invention. Changes therein and other uses will occur to those skilled in the art which are encompassed within the spirit of the invention as defined by the scope of the claims.

What is claimed is:

1. A dynamic alarm system comprising:
   a housing;
   an electronic processor;
   a microphone electronically coupled to the electronic processor, the microphone configured to sense an ambient noise level proximal to the housing;
   a user interface on the housing and electronically coupled to the electronic processor, the user interface configured to allow a user to select a signal-to-noise ratio based on the ambient noise level; and
   a speaker electronically coupled to the electronic processor, the speaker configured to output an audible tone according to the selected signal-to-noise ratio when a physiological parameter detected by a sensor coupled to a patient exceeds a preselected threshold for that physiological parameter.

2. The system of claim 1, wherein the housing includes a port configured to receive data from the sensor.

3. The system of claim 1, wherein the physiological parameter is blood pressure, heart rate, electrocardiogram signal, or blood oxygen saturation.

4. The system of claim 1, wherein the electronic processor is configured to control power to the speaker to control an alarm volume based on the selected signal-to-noise-ratio.

5. The system of claim 4, wherein the alarm volume is less than the ambient noise level.

6. The system of claim 4, wherein the alarm volume is greater than the ambient noise level.

7. The system of claim 1, wherein the signal-to-noise-ratio is between −11 dB and +4 dB.

8. The system of claim 1, wherein the speaker output is between 33 dB and 81 dB.

9. The system of claim 8, wherein the microphone input is between 50 dB and 90 dB.

10. A dynamic alarm system comprising:
    a microphone configured to sense an ambient noise volume of an area around the alarm system;
    a speaker; and
    an electronic processor configured to
       determine an alarm volume based on a negative signal-to-noise-ratio wherein the signal is the alarm volume and the noise is the ambient noise volume, and
       control power supplied to the speaker to control the alarm volume when the electronic processor receives a triggering signal from a sensor coupled to a patient, wherein the triggering signal indicates that a physiological parameter has exceeded a preselected threshold.

11. The system of claim 10, further comprising a user interface configured to receive input to adjust settings of the alarm system to increase or decrease the signal-to-noise-ratio of an emitted alarm.

12. The system of claim 10, wherein the speaker output is between 33 dB and 81 dB.

13. The system of claim 12, wherein the microphone input is between 50 dB and 90 dB.

14. The system of claim 10, wherein the physiological parameter is blood pressure, heart rate, electrocardiogram signal, or blood oxygen saturation.

* * * * *